(12) United States Patent
Ganton et al.

(10) Patent No.: US 10,750,620 B2
(45) Date of Patent: Aug. 18, 2020

(54) FLEXIBLE CIRCUIT BATTERY ATTACHMENT DEVICES, SYSTEMS, AND METHODS

(71) Applicant: Capsule Technologies, Inc., San Diego, CA (US)

(72) Inventors: Robert Ganton, San Diego, CA (US); Robert Ballam, Eatons Hill (AU)

(73) Assignee: PHILIPS HEALTHCARE INFORMATICS, INC., Cambridge, MA (US)

(*) Notice: Subject to any disclaimer, the term of this patent is extended or adjusted under 35 U.S.C. 154(b) by 234 days.

(21) Appl. No.: 15/839,625

(22) Filed: Dec. 12, 2017

(65) Prior Publication Data

US 2018/0177061 A1 Jun. 21, 2018

Related U.S. Application Data

(60) Provisional application No. 62/436,910, filed on Dec. 20, 2016.

(51) Int. Cl.
*H05K 3/32* (2006.01)
*A61N 1/375* (2006.01)
(Continued)

(52) U.S. Cl.
CPC ............. *H05K 3/323* (2013.01); *A61N 1/375* (2013.01); *H01M 2/026* (2013.01); *H05K 1/118* (2013.01);
(Continued)

(58) Field of Classification Search
CPC .... H05K 1/18; H05K 1/187–189; H05K 3/10; H01Q 1/27; H01Q 1/273; A61B 5/04; A61B 5/0442; A61B 5/01
(Continued)

(56) References Cited

U.S. PATENT DOCUMENTS

| 4,064,552 A | 12/1977 | Angelucci et al. |
| 5,153,710 A | 10/1992 | McCain |

(Continued)

FOREIGN PATENT DOCUMENTS

EP 2 387 088 A2 11/2011

OTHER PUBLICATIONS

Kutbee et al., "Flexible and biocompatible high-performance solid-state micro-battery for implantable orthodontic system," NPJ Flexible Electronics, vol. 1, No. 1, Oct. 25, 2017, XP055453476, DOI: 10.1038/s41528-017-0008-7, see figures 1-5; items of figure 1(a) and (b) as well as of figure 4(a), (b), (c), 8 pages.

(Continued)

*Primary Examiner* — Tuan T Dinh

(57) ABSTRACT

Disclosed are systems, devices, and methods for connecting a flexible circuit to a battery. Conductive pads are formed simultaneously with mounting and reflowing circuitry components on a flexible circuit, where the conductive pads serve as preformed tabs capable of being joined to terminals of a battery. The flexible circuit can be bent in a manner so that the conductive pads are positioned adjacent to the positive and negative terminals of a battery, such as a coin cell battery. The conductive pads can be attached to the terminals to form a cost-efficient and space-efficient design connecting the battery to the flexible circuit.

18 Claims, 5 Drawing Sheets

(51) Int. Cl.
*H05K 1/14* (2006.01)
*H01M 2/02* (2006.01)
*H05K 1/11* (2006.01)
*H01R 12/59* (2011.01)
*H05K 1/18* (2006.01)
*A61N 1/378* (2006.01)

(52) U.S. Cl.
CPC .............. *H05K 1/147* (2013.01); *H05K 3/328* (2013.01); *A61N 1/378* (2013.01); *H01L 2224/2402* (2013.01); *H01R 12/59* (2013.01); *H05K 1/189* (2013.01); *H05K 2201/056* (2013.01); *H05K 2201/10037* (2013.01)

(58) Field of Classification Search
USPC .................. 361/749–750, 775–784, 803; 174/254–264
See application file for complete search history.

(56) References Cited

U.S. PATENT DOCUMENTS

| | | | | |
|---|---|---|---|---|
| 5,931,693 A * | 8/1999 | Yamazaki | ........... | H01M 2/1044 429/96 |
| 5,931,764 A * | 8/1999 | Freeman | .................. | G04G 9/00 361/679.03 |
| 6,208,521 B1 * | 3/2001 | Nakatsuka | .......... | H01L 23/5387 174/254 |
| 6,245,092 B1 * | 6/2001 | Schaldach, Jr. | ........ | H05K 1/118 607/1 |
| 6,711,024 B1 * | 3/2004 | Johansson | .............. | H05K 1/189 361/760 |
| 7,211,884 B1 | 5/2007 | Davis et al. | | |
| 7,856,705 B2 | 12/2010 | Degieux et al. | | |
| 8,460,026 B2 | 6/2013 | Tate et al. | | |
| 8,634,204 B2 | 1/2014 | Rothkopf et al. | | |
| 8,765,284 B2 | 7/2014 | Tucholski | | |
| 9,114,258 B2 * | 8/2015 | Escribano | ........... | A61N 1/0456 |
| 2007/0088419 A1 * | 4/2007 | Fiorina | ................ | A61N 1/0476 607/152 |
| 2012/0310070 A1 * | 12/2012 | Kumar | ............... | A61B 5/04085 600/391 |
| 2014/0206977 A1 * | 7/2014 | Bahney | ................. | A61B 5/721 600/391 |
| 2015/0064516 A1 * | 3/2015 | Swoish | ................ | H01M 2/206 429/61 |
| 2016/0149292 A1 * | 5/2016 | Ganton | .................... | A61B 5/01 600/300 |
| 2017/0290535 A1 | 10/2017 | Rao et al. | | |

OTHER PUBLICATIONS

International Search Report and Written Opinion for PCT/US2017/066080 dated Mar. 6, 2018, all pages.
International Preliminary Report on Patentability for PCT/US2017/066080 dated Jun. 25, 2019, all pages.

* cited by examiner

FLEXIBLE CIRCUIT BATTERY ATTACHMENT DEVICES, SYSTEMS, AND METHODS

PRIORITY CLAIM

This application claims priority to U.S. Provisional Patent Application No. 62/436,910, entitled "FLEXIBLE CIRCUIT BATTERY ATTACHMENT DEVICES, SYSTEMS, AND METHODS," and filed on Dec. 20, 2016, which is hereby incorporated by reference in its entirety and for all purposes.

TECHNICAL FIELD

This disclosure relates generally to connecting a flexible circuit to a battery, and more particularly, to conductive pads on a flexible circuit for connecting to terminals on a battery.

DESCRIPTION OF RELATED TECHNOLOGY

Many electronic devices are becoming smaller, lighter, thinner, and cheaper. Circuitry for such electronic devices may be formed on printed circuit boards (PCBs) or printed wiring boards (PWBs), and may be powered by batteries. Coin cell batteries may be useful for their low self-discharge rates, high energy density, and low cost. Also, coin cell batteries are often used to lower the cost and reduce the size of the electronic devices. However, conventional methods for connecting or attaching a battery to circuitry of an electronic device may increase the size and cost of the electronic device. In some instances, the battery attachment or connection method may be more costly than or just as costly as the battery itself.

SUMMARY

The devices and methods of this disclosure each have several aspects, no single one of which is solely responsible for the desirable attributes disclosed herein.

One aspect of the subject matter of this disclosure can be implemented in a system including a battery and a flexible circuit. The battery has a positive terminal and a negative terminal. The flexible circuit includes a first conductive pad and a second conductive pad, and the flexible circuit is oriented to contact the first conductive pad to the positive terminal and the second conductive pad to the negative terminal of the battery.

In some implementations, the first conductive pad and the second conductive pad include a first surface mount technology (SMT) bond pad and a second SMT bond pad, respectively, attached to the flexible circuit. The first SMT bond pad is directly bonded to the positive terminal of the battery and the second SMT bond pad is directly bonded to the negative terminal of the battery. In some implementations, the first conductive pad and the second conductive pad are symmetric about an axis of symmetry dividing the flexible circuit into two congruent halves. In some implementations, the first conductive pad and the second conductive pad cover one or more holes in the flexible circuit. In some implementations, the flexible circuit includes a microprocessor and one or more circuitry components, where the first conductive pad, the second conductive pad, the microprocessor, and the one or more circuitry components are formed on a surface of the flexible circuit that is inwardly facing towards the battery. In some implementations, each of the first and second conductive pads includes a solder material. In some implementations, the one or more conductive pads include a first conductive pad and a second conductive pad, each of the first conductive pad and the second conductive pad is soldered to the flexible circuit and welded to the battery to form connections with the positive terminal and the negative terminal, respectively. In some implementations, the battery includes a coin cell battery.

Another innovative aspect of the subject matter described in this disclosure can be implemented in a system. The system includes a battery having a positive terminal and a negative terminal, a flexible circuit having one or more holes, a first SMT bond pad soldered on the flexible circuit and directly bonded to the positive terminal of the battery, and a second SMT bond pad soldered on the flexible circuit and directly bonded to the negative terminal of the battery. The first and the second SMT bond pads cover the one or more holes in the flexible circuit.

In some implementations, the first SMT bond pad is resistance welded to the positive terminal of the battery and the second SMT bond pad is resistance welded to the negative terminal of the battery. In some implementations, the flexible circuit is folded in a shape so that the first SMT bond pad and the second SMT bond pad are inwardly facing towards the battery.

Another innovative aspect of the subject matter described in this disclosure can be implemented in a method of connecting a flexible circuit to a battery. The method includes forming a first conductive pad and a second conductive pad on a flexible circuit, orienting the flexible circuit to position the first conductive pad adjacent to and contacting a positive terminal of a battery and the second conductive pad adjacent to and contacting a negative terminal of the battery, and joining the first conductive pad to the positive terminal of the battery and the second conductive pad to the negative terminal of the battery.

In some implementations, the flexible circuit includes one or more surface mount devices (SMDs) and a microprocessor, where the method further includes reflowing the first conductive pad, the second conductive pad, the microprocessor, and the one or more SMDs to bond the first conductive pad, the second conductive pad, the microprocessor, and the one or more SMDs to the flexible circuit. In some implementations, the first conductive pad and the second conductive pad are formed on the flexible circuit simultaneous with the one or more SMDs and the microprocessor. Reflowing the first conductive pad, the second conductive pad, the microprocessor, and the one or more SMDs can occur at a temperature equal to or greater than about 150° C. In some implementations, joining the first conductive pad to the positive terminal and the second conductive pad to the negative terminal includes a process selected from the group consisting of: laser welding, arc welding, and resistance welding. In some implementations, the flexible circuit is bent in a U-shape so that the first conductive pad and the second conductive pad are inwardly facing towards the battery. In some implementations, forming the first conductive pad and the second conductive pad on the flexible circuit includes mounting the first conductive pad and the second conductive pad on the flexible circuit using a pick-and-place machine. In some implementations, the flexible circuit includes one or more holes, where forming the first conductive pad and the second conductive pad includes covering the one or more holes with the first conductive pad and the second conductive pad.

BRIEF DESCRIPTION OF THE DRAWINGS

The accompanying drawings, which are incorporated herein and constitute part of this specification, illustrate exemplary embodiments of the claims, and together with the general description given above and the detailed description given below, serve to explain the features of the claims.

Like reference numbers and designations in the various drawings indicate like elements.

DETAILED DESCRIPTION

Figure 1A:
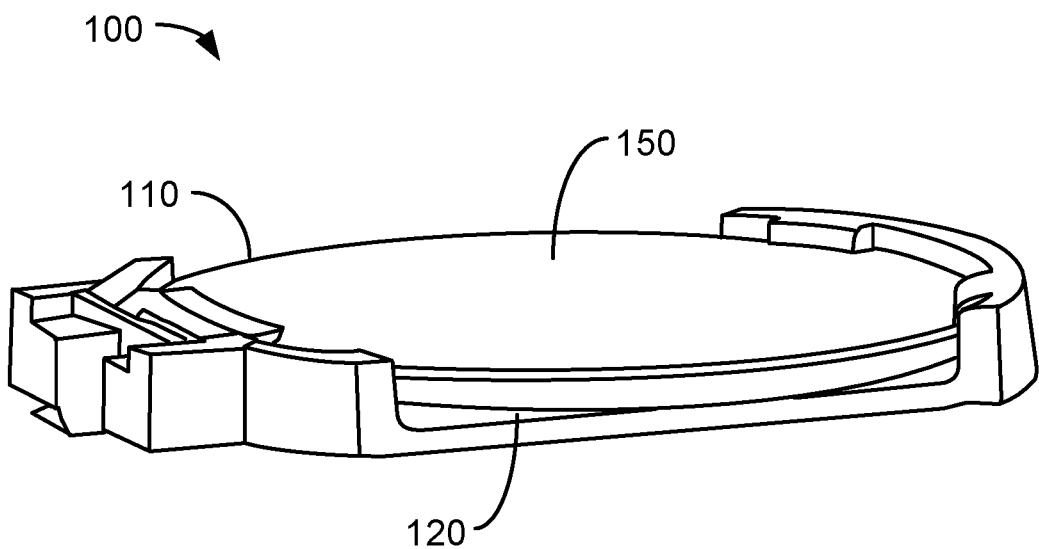
FIG. 1A shows a perspective view of an example battery holder retaining a battery.

Various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the claims.

The described implementations may be implemented in any electronic device, apparatus, or system powered by a battery. More particularly, it is contemplated that the described implementations may be included in or associated with a variety of electronic devices such as, but not limited to: biomedical devices, biometric devices, sensors, mobile telephones, multimedia Internet enabled cellular telephones, mobile television receivers, wireless devices, smartphones, Bluetooth® devices, personal data assistants (PDAs), wireless electronic mail receivers, hand-held or portable computers, netbooks, notebooks, smartbooks, tablets, printers, copiers, scanners, facsimile devices, global positioning system (GPS) receivers/navigators, cameras, digital media players (such as MP3 players), camcorders, game consoles, wrist watches, clocks, calculators, television monitors, flat panel displays, electronic reading devices (such as e-readers), computer monitors, auto displays (including odometer and speedometer displays, etc.), cockpit controls or displays, camera view displays (such as the display of a rear view camera in a vehicle), electronic photographs, electronic billboards or signs, projectors, architectural structures, microwaves, refrigerators, stereo systems, cassette recorders or players, DVD players, CD players, VCRs, radios, portable memory chips, washers, dryers, washer/dryers, parking meters, packaging (such as in electromechanical systems (EMS) applications including microelectromechanical systems (MEMS) applications, as well as non-EMS applications), aesthetic structures (such as display of images on a piece of jewelry or clothing) and a variety of EMS devices. The teachings herein also can be used in non-display applications such as, but not limited to, electronic switching devices, radio frequency filters, sensors, accelerometers, gyroscopes, motion-sensing devices, magnetometers, inertial components for consumer electronics, parts of consumer electronics products, varactors, liquid crystal devices, electrophoretic devices, drive schemes, manufacturing processes and electronic test equipment. Thus, the teachings are not intended to be limited to the implementations depicted solely in the Figures, but instead have wide applicability as will be readily apparent to one having ordinary skill in the art.

The present disclosure relates generally to systems, devices, and methods for connecting a flexible circuit to a battery. Conductive pads may be formed simultaneously with circuitry on a flexible circuit. In some implementations, the conductive pads and the circuitry may undergo surface mount technology (SMT) processes and infrared (IR) reflow processes to form the conductive pads and the circuitry on the flexible circuit. The flexible circuit may be oriented about one or more axes so that one of the conductive pads is positioned adjacent to a positive terminal of the battery and another one of the conductive pads is positioned adjacent to a negative terminal of the battery. The conductive pads may be joined to the positive and negative terminals of the battery. For example, the conductive pads may be joined by laser welding or resistance welding.

Particular implementations of the subject matter described in this disclosure can be implemented to realize one or more of the following potential advantages. Conductive pads on a flexible circuit for attaching to a battery may reduce costs compared to typical battery attachment methods. The cost associated with conductive pads on a flexible circuit for battery attachment may be cheaper than using conventional battery holders and pre-attached tabs on a battery. Cost of manufacturing and ease of manufacturing may also be improved by integrating the formation of the conductive pads with circuitry on the flexible circuit, whereas adding a conventional battery holder or attaching tabs to a battery increases costs, complexity, and number of operations. Conductive pads on a flexible circuit for attaching to a battery may also enable a more compact package and reduce form factor because the flexible circuit can be bent, folded, shaped, or otherwise oriented to connect the conductive pads to terminals of the battery. Incorporating a conventional battery holder to a circuit board or adding pre-attached tabs on a battery, however, increases the volume of a final product. Furthermore, the flexible circuit may be attached to the battery without using an adhesive that may degrade over time and without having to continuously apply mechanical pressure. The flexible circuit may be attached to the battery using localized heating techniques that minimize or avoid damaging the battery and surrounding circuitry. The present disclosure for connecting a battery to a flexible circuit may generate savings in size, volume, manufacturing steps, and cost of the final product.

A conventional technique for attaching a battery to circuitry on a PCB or PWB may involve a battery holder. Battery holders are used to constrain a battery and provide electrical contact to terminals of the battery. Battery holders may be incorporated with an electronic device and may provide electrical connection to various components and circuitry of the electronic device. Generally, battery holders are expensive, bulky, and take up a significant volume of space in the electronic device. Furthermore, battery holders may not be compatible with flexible circuits because typical battery holders are rigid and are more suitable for rigid PCBs and PWBs.

Figure 1B:
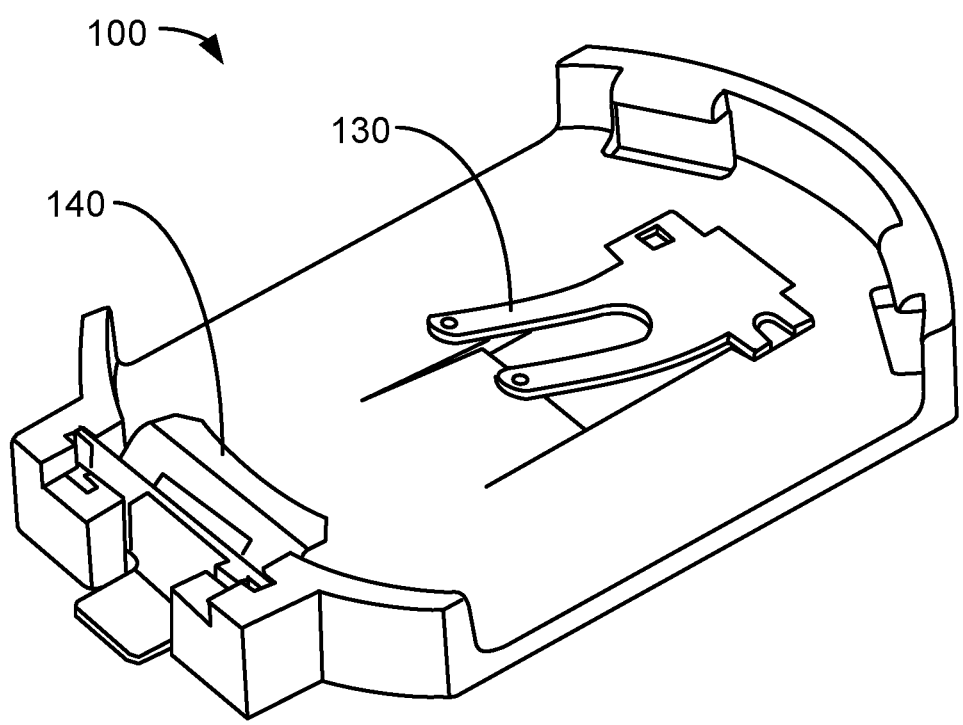
FIG. 1B shows a perspective view of the battery holder of FIG. 1A without a battery retained in the battery holder.

FIG. 1A shows a perspective view of an example battery holder retaining a battery. FIG. 1B shows a perspective view of the battery holder of FIG. 1A without a battery retained in the battery holder. The battery holder 100 can have a cavity that is sized and shaped to accommodate a battery 150. The battery 150 may be removably inserted into the cavity of the battery holder 100 and retained in the battery holder 100. The battery holder 100 can include electrically conductive tabs 130, 140 configured to contact a positive terminal 110 of the battery and a negative terminal 120 of the battery 150. The electrically conductive tabs 130, 140 can be metal tabs or clips that mechanically secure the battery 150 in place and help provide electrical connection to a PCB or PWB. As shown in FIG. 1B, a first electrically conductive tab 130 is positioned on a bottom surface of the battery holder 100 and a second electrically conductive tab 140 inwardly extends from a side of the battery holder 100. Each of the electrically conductive tabs 130, 140 in FIGS. 1A and 1B may contact a positive terminal 110 or a negative terminal 120 of a battery 150, such as a coin cell battery as shown in FIG. 1A. As used herein, coin cell batteries may also be referred to as "button cell" batteries or "watch" batteries.

Another conventional technique for attaching or connecting a battery to circuitry on a PCB or PWB may utilize pre-attached tabs on the battery. Typically, purchasing a battery with pre-attached tabs is expensive, and even pre-attaching tabs manually to terminals of a battery is an expensive process. Having tabs on a battery requires multiple manual assembly steps, including assembly steps of soldering the tabs onto the battery and subsequently soldering the tabs to the PCB or PWB, that add to the cost and difficulty of manufacturing. In addition, the tabs usually extend from the battery in a manner that increases the size of the final package. For example, the tabs may extend from the battery by more than 3 mm, more than 5 mm, or between 5 mm and 10 mm. Moreover, tabs on a battery are difficult to join (e.g., weld) to a flexible circuit and restrict the way they can be attached to a flexible circuit.

Figure 2:
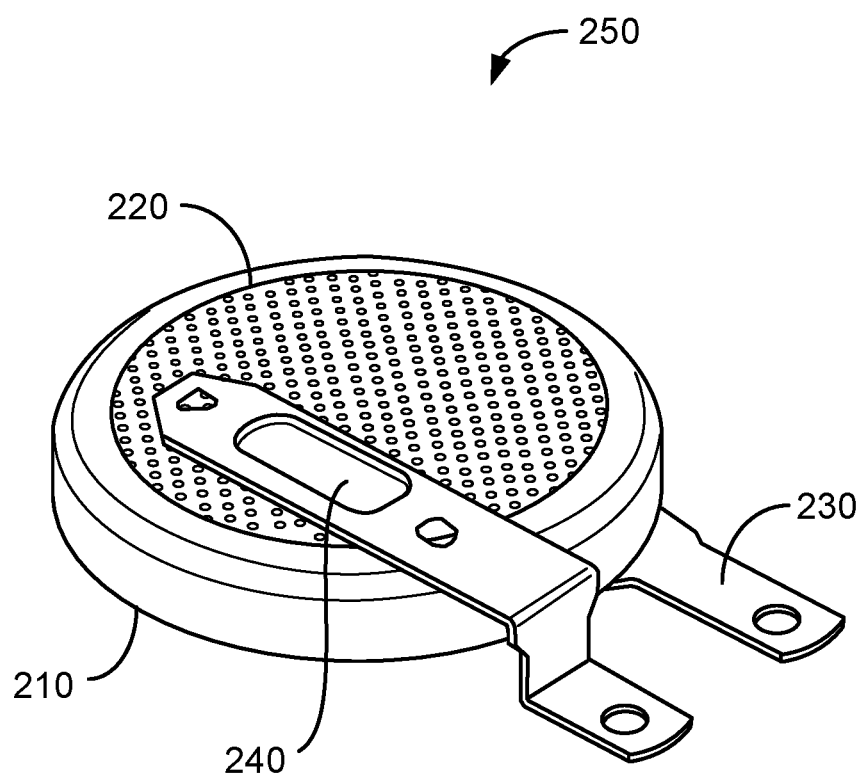
FIG. 2 shows a perspective view of example coin cell battery with pre-attached tabs.

FIG. 2 shows a perspective view of example coin cell battery with pre-attached tabs. A coin cell battery 250 includes tabs 230, 240 that are electrically conductive, where the first tab 230 extends from a bottom surface of the coin cell battery 250 and the second tab 240 extends from a top surface of the coin cell battery 250. As shown in FIG. 2, a first tab 230 is connected to a positive terminal 210 of the coin cell battery 250 and a second tab 240 is connected to a negative terminal 220 of the coin cell battery 250. Where the first tab 230 and the second tab 240 extend from the coin cell battery 250 with exposed surfaces, the first tab 230 and the second tab 240 may be capable of being attached to a PCB or PWB (not shown). Examples of techniques for attaching to a PCB or PWB include soldering and welding. In some implementations, each of the first tab 230 and the second tab 240 may include nickel, tin, steel, copper, aluminium, nickel-plated copper, nickel-plated steel, copper-plated aluminium, and combinations thereof. In some implementations, each of the first tab 230 and the second tab 240 may be joined or attached to the coin cell battery 250 by a technique known in the art such as soldering or welding. It will be understood that tabs 230, 240 may be formed not only on coin cell batteries as shown in FIG. 2, but may be formed on batteries of different shapes and sizes, including cylindrical batteries, rectangular batteries, etc.

The present disclosure forms conductive pads on a flexible circuit, where the conductive pads are arranged on the flexible circuit to connect or attach to terminals of a battery. Rather than attaching tabs directly on a battery that requires additional manual assembly, conductive pads on a flexible circuit are formed without the labor and costs associated with manually attaching tabs on a battery. In addition, conductive tabs on a flexible circuit are less bulky and rigid than conventional battery holders. In some implementations, the conductive pads are formed during automated operations for forming a microprocessor and other circuitry on the flexible circuit. Specifically, for example, the conductive pads are formed on the flexible circuit using standard SMT processes and IR reflow processes that are also used to form the microprocessor and other circuitry on the flexible circuit. In some implementations, the conductive pads are SMT bond pads on the flexible circuit that are directly bonded to terminals of the battery.

Figure 3A:
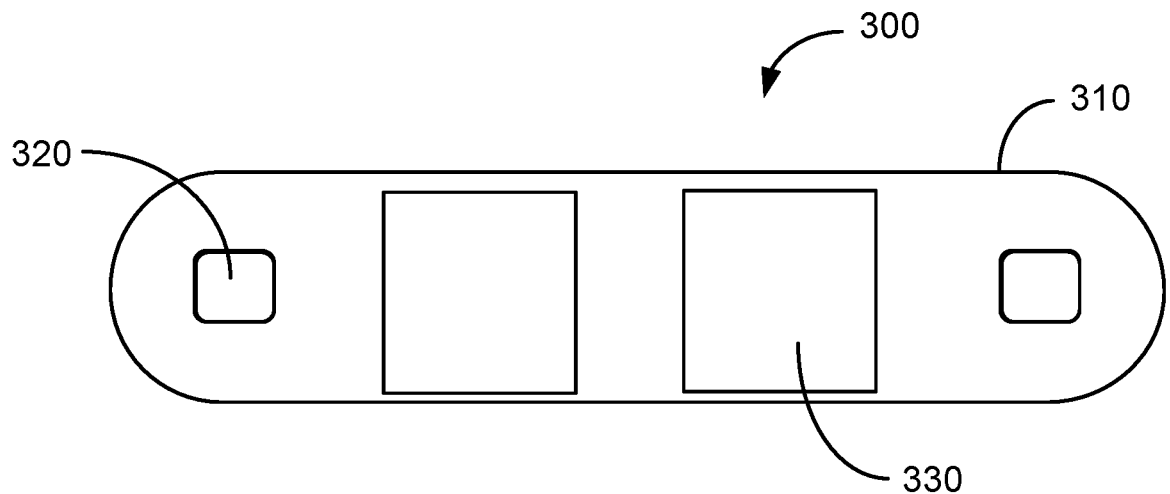
FIG. 3A shows a top plan view illustrating a schematic diagram representation of an example flexible circuit with holes on opposite sides of the flexible circuit according to some implementations.
Figure 3B:
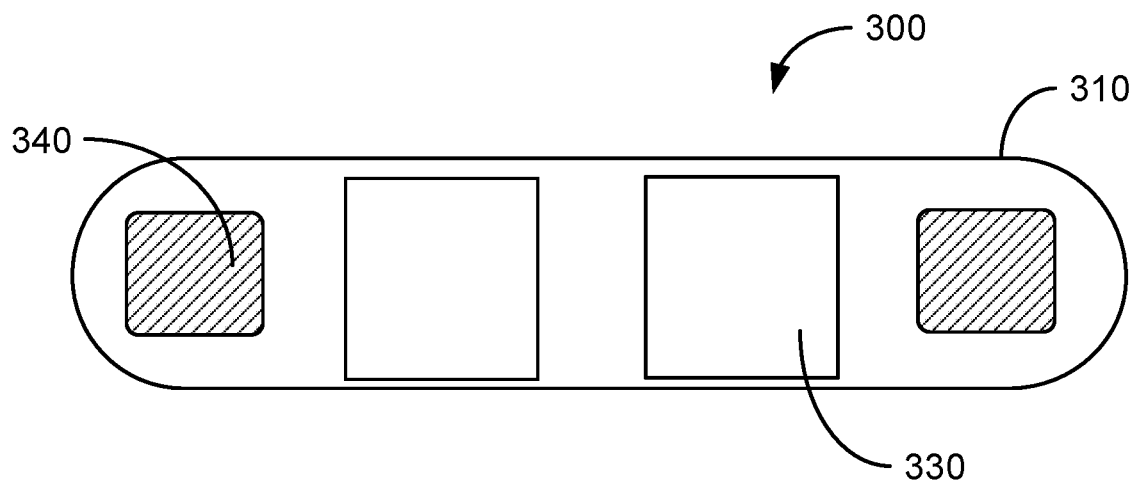
FIG. 3B shows a top plan view illustrating a schematic diagram representation of the flexible circuit of FIG. 3A with conductive pads covering the holes of the flexible circuit according to some implementations.
Figure 3C:
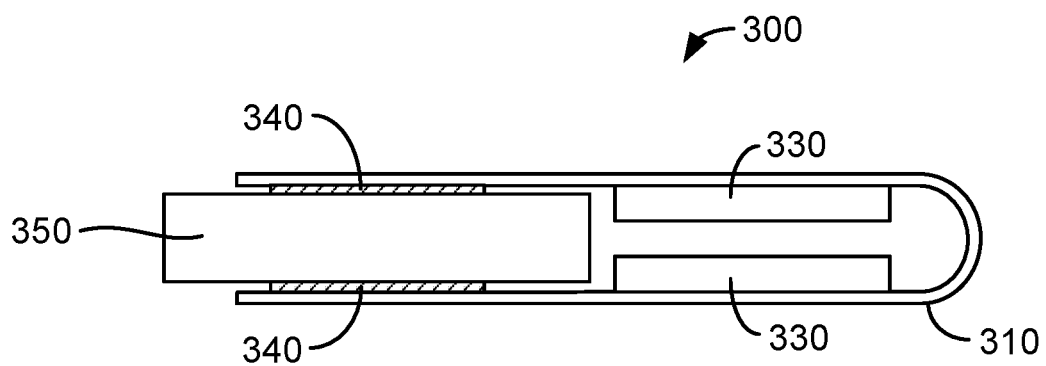
FIG. 3C shows a side view illustrating a schematic diagram representation of the flexible circuit of FIG. 3B with the conductive pads folded over to connect to terminals of a battery according to some implementations.

FIGS. 3A-3C illustrate various stages of an example process for fabricating a flexible circuit and attaching the flexible circuit to a battery. It will be understood that a flexible circuit may also be referred to as a "flex circuit" or simply "flex." It will be understood that the battery can be any battery having a positive terminal and a negative terminal, such as a coin cell battery. The flexible circuit can include a flexible substrate capable of bending about one or more axes. Specifically, the flexible substrate is capable of conforming to a desired shape or at least flexing during normal use. In some implementations, the flexible substrate can be made out of a polymer, such as polyimide or polyetheretherketone (PEEK).

FIG. 3A shows a top plan view illustrating a schematic diagram representation of an example flexible circuit with holes on opposite sides of the flexible circuit according to some implementations. FIG. 3A shows the flexible circuit 300 prior to bending, folding, or shaping. Though the flexible circuit 300 has at least a front surface and a rear surface, the diagram representation in FIG. 3A depicts only one of the surfaces of the flexible circuit 300. The flexible circuit 300 can have a generally rectangular shape with curved edges on the right-hand side and the left-hand side, though it will be understood that the flexible circuit can have any desired geometric shape. In some implementations, the flexible circuit 300 can be symmetric about one or more axes.

The flexible circuit 300 can include a flexible substrate 310 on which various components or holes are formed. The flexible substrate 310 can include one or more areas designated for circuitry 330. The one or more areas designated for circuitry 330 may be on the front surface, the rear surface, or both the front and rear surfaces of the flexible circuit 300. One or more surface mount devices (SMDs), processors, and other circuitry may be attached to or formed on the flexible circuit 300 in the one or more areas designated for circuitry 330. For example, a microprocessor may be attached to or formed on the flexible circuit 300 in the one or more areas designated for circuitry 330. As shown in FIG. 3A, one area for circuitry is provided on a right-hand side and another area for circuitry is provided on a left-hand side of the flexible circuit 300.

Holes 320 may be formed on opposite sides of the flexible circuit 300. The holes 320 may extend through the flexible substrate 310, meaning that the holes 320 extend from a front surface to a rear surface of the flexible substrate 310. In some implementations, the holes 320 may be formed on opposite sides about an axis of symmetry dividing the flexible circuit 300 into two congruent halves. Each hole 320 may be sized and shaped to accommodate a conductive pad. In some implementations, the holes 320 may be sized and shaped to allow resistance welding probes to join conductive pads to terminals of a battery.

FIG. 3B shows a top plan view illustrating a schematic diagram representation of the flexible circuit of FIG. 3A with conductive pads covering the holes of the flexible circuit according to some implementations. The conductive pads 340 may be formed on the flexible substrate 310 of the flexible circuit 300. The conductive pads 340 are configured to be joined to terminals of a battery. Though the conductive pads 340 are shown as rectangular plates, it will be understood that the conductive pads 340 can have any suitable geometry for covering the holes 320 and connecting to terminals of a battery. On one of the surfaces of the flexible circuit 300, conductive pads 340 may be mounted, placed, disposed, or positioned over the holes 320. With the conductive pads 340 covering the holes 320, the conductive pads 340 are exposed on the front surface and the rear surface of the flexible substrate 310.

In some implementations, each of the conductive pads 340 may include a solder material. Solder material can include but is not limited to aluminium, nickel, copper, tin, bismuth, silver, gold, zinc, lead, antimony, and alloys thereof. In some implementations, the solder material of the conductive pads 340 connect to the flexible circuit 300.

The conductive pads 340 may include a first conductive pad and a second conductive pad. Though FIG. 3B shows two conductive pads 340, it will be understood that the flexible circuit 300 may include additional conductive pads 340. The conductive pads 340 are positioned on opposite sides of the flexible circuit 300 and, as shown in FIG. 3B, the conductive pads 340 are positioned on opposite sides about an axis of symmetry dividing the flexible circuit 300 into two congruent halves. In some implementations, the process for mounting the conductive pads 340 over the holes 320 can be machine-assisted. For example, the conductive pads 340 may be mounted by an automated operation using a pick-and-place machine. The conductive pads 340 may be mounted or positioned by an automated operation simultaneous with mounting or positioning SMDs and other circuitry in the one or more designated areas for circuitry 330. Accordingly, SMDs, circuitry, and conductive pads 340 may undergo the same process for mounting and positioning on the flexible circuit 300. In some implementations, the conductive pads 340 are SMT bond pads.

The conductive pads 340 may be attached on the flexible circuit 300 by the same process for attaching the SMDs and/or circuitry on the flexible circuit 300. In some implementations, the conductive pads 340 may undergo a reflow operation, such as an IR reflow operation. SMDs and/or circuitry in the one or more designated areas for circuitry 330 may simultaneously undergo the same reflow operation. The reflow operation may heat the conductive pads 340 at a temperature equal to or greater than 150° C., equal to or greater than 200° C., equal to or greater than 250° C., equal to or greater than 300° C., or between about 150° C. and about 500° C. This causes the conductive pads 340 to be bonded to the flexible circuit 300. The conductive pads 340 may be attached to the flexible circuit 300 by solder material after the IR reflow operation. In some implementations, the reflow operation heats the conductive pads 340 in a linear oven.

At such high temperatures, batteries are adversely affected and so batteries generally cannot withstand reflow operations. If a battery were attached to the flexible circuit 300 prior to reflow operations, SMDs and other circuit components would be activated and would be adversely affected during the reflow operation. Most electronics typically cannot handle temperatures greater than 100° C. Therefore, batteries with or without pre-attached tabs are not suitable for reflow operations. However, conductive pads 340 configured to attach to terminals of a battery are suitable for automated mounting and reflow operations.

FIG. 3C shows a side view illustrating a schematic diagram representation of the flexible circuit of FIG. 3B folded over to connect the conductive pads to terminals of a battery according to some implementations. The flexible circuit 300 is capable of bending or folding to a desired shape after mounting and attaching circuitry on the flexible circuit 300. A battery 350, such as a coin cell battery, may be positioned adjacent to at least one of the surfaces of the flexible circuit 300. The battery 350 has a positive terminal (anode) and a negative terminal (cathode). The flexible circuit 300 is bent so as to contact the positive terminal of the battery 350 to one of the conductive pads 340 and contact the negative terminal of the battery 350 to another one of the conductive pads 340. In FIG. 3C, the flexible circuit 300 is folded over and around a portion of the battery 350 so that the conductive pads 340 inwardly face towards the battery 350. The flexible circuit 300 may be folded in a manner to form a U-shape. In FIG. 3C, SMDs and other circuit components formed in the one or more designated areas for circuitry 330 of the flexible circuit 300 may be inwardly facing towards the battery 350.

The conductive pads 340 may be joined to the terminals of the battery 350. In some implementations, the conductive pads 340 include SMT bond pads on the flexible circuit 300 that are directly bonded to the terminals of the battery 350. In some implementations, the conductive pads 340 are connected or otherwise attached to the terminals of a battery 350 by a weld. For example, each of the conductive tabs 340 may be laser-welded, arc-welded, or resistance-welded to join the conductive tabs 340 to the terminals of the battery 350. A resistance weld probe may be inserted through the one or more holes 320 to join the conductive pads 340 to the terminals of the battery 350. The resistance weld probe may provide localized heating by applying a very high current so that the conductive pads 340 (e.g., SMT bond pads) form a bond with the battery 350. This fixedly connects the battery 350 to the flexible circuit 300. Thus, the conductive pads 340 may have one or more spot welds connecting the conductive pads 340 to the terminals of the battery 350.

The conductive pads 340 may be connected to the flexible circuit 300 by one or more solder joints and may be connected to the terminals of the battery 350 by one or more welds. Accordingly, the conductive pads 340 may include one or more materials capable of attaching to a flexible circuit 300 through a reflow operation and capable of attaching to terminals of a battery 350 through a welding operation. The attached battery 350 forms a compact design at a low-cost, where attachment is accomplished with minimal or few manual assembly operations, and where attachment is accomplished with minimal or no damage to the battery 350 and surrounding circuitry.

In some implementations, the conductive pads 340 connected to the battery 350 by one or more welds without soldering and without applying an adhesive. Soldering generally transfers heat in an amount and over a duration that degrades the battery 350 and potentially degrades other surrounding circuitry. Soldering may also degrade the flexible circuit 300 and cause the flexible circuit 300 to warp. An adhesive, such as a conductive adhesive, may not be reliable in retaining the battery 350 and may peel apart over time.

However, laser welding, arc welding, resistance welding, and other suitable welding techniques directly bond the conductive pads 340 to the battery 350 while minimizing or avoiding damage to the battery 350, the flexible circuit 300, and other surrounding circuitry.

A system of the present disclosure can include a battery with a positive terminal and a negative terminal, and a flexible circuit bent, folded, or oriented in a shape so that a first conductive pad contacts the positive terminal and a second conductive pad contacts the negative terminal. The first and the second conductive pads may be joined to the terminals of the battery. In some implementations, the battery is a coin cell battery. In some implementations, the flexible circuit further includes SMDs and other circuitry, such as a microprocessor. In some implementations, the first and second conductive pads cover one or more holes in the flexible circuit. In some implementations, the first and second conductive pads are welded to the terminals of the battery. Examples of welds for joining the conductive pads include but are not limited to laser welds, arc welds, and resistance welds. In some implementations, the flexible circuit is bent in a U-shape around a portion of the battery.

Figure 4:
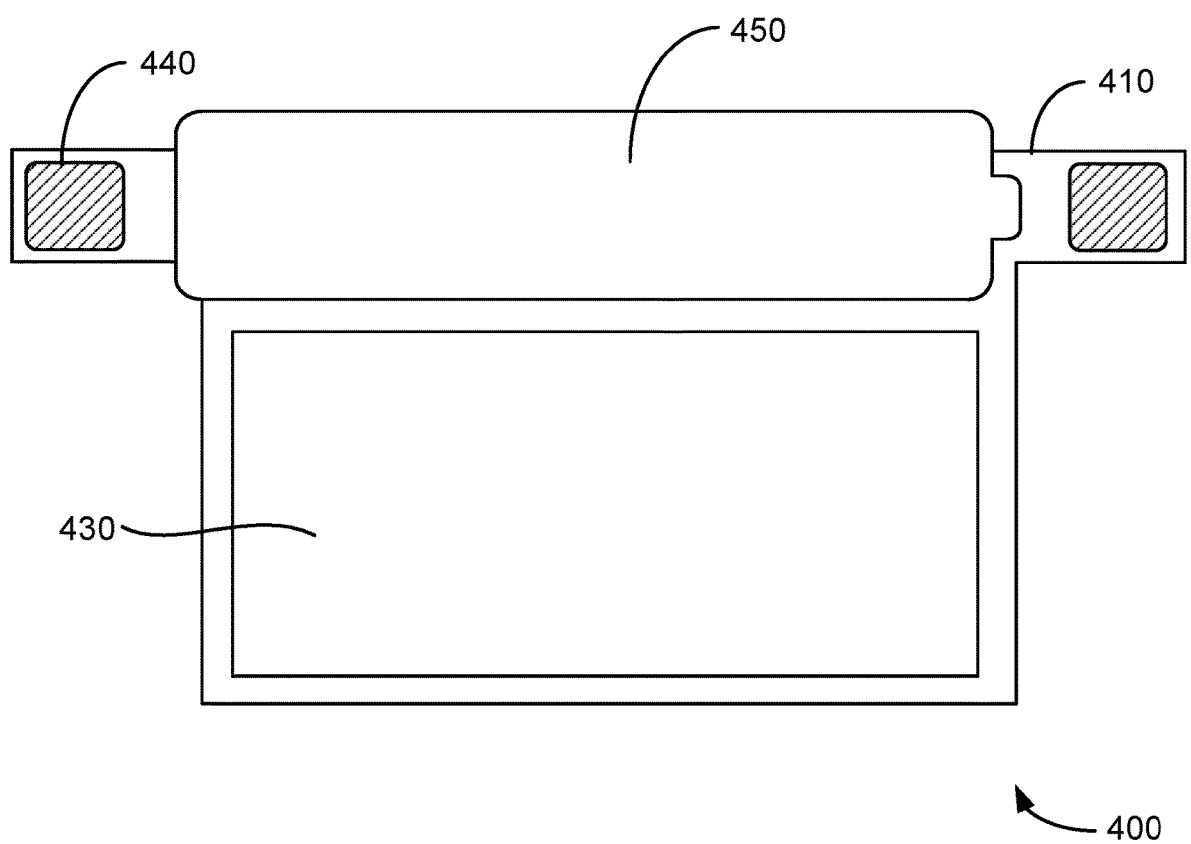
FIG. 4 shows a top plan view illustrating a schematic diagram representation of an example flexible circuit with conductive pads for connecting to a cylindrical battery according to some implementations.

The battery attachment method of the present disclosure is not limited to coin cell batteries, but may also include batteries of other shapes and sizes. For example, the battery attachment method of the present disclosure may be utilized with cylindrical batteries such as AA or AAA batteries. FIG. 4 shows a top plan view illustrating a schematic diagram representation of an example flexible circuit with conductive pads for connecting to a cylindrical battery according to some implementations. A flexible circuit 400 may be assembled so that conductive pads 440 are formed on the flexible circuit 400 simultaneous with SMDs and other circuitry 430. The conductive pads 440 may be SMT bond pads on the flexible circuit 400. The conductive pads 440 and the circuitry 430 may be formed on a flexible substrate 410 of the flexible circuit 400. The conductive pads 440 may be positioned on opposite sides of the flexible circuit 400. In FIG. 4, a cylindrical battery 450 is positioned between the conductive pads 440. The flexible circuit 400 may be capable of orienting or conforming to a shape so that one of the conductive pads 440 contacts a negative terminal of the cylindrical battery 450 and another one of the conductive pads 440 contacts a positive terminal of the cylindrical battery 450. In FIG. 4, a conductive pad 440 on the left-hand side can be positioned adjacent to the negative terminal of the cylindrical battery 450, and another conductive pad 440 on the right-hand side can be positioned adjacent to the positive terminal of the cylindrical battery 450.

Figure 5:
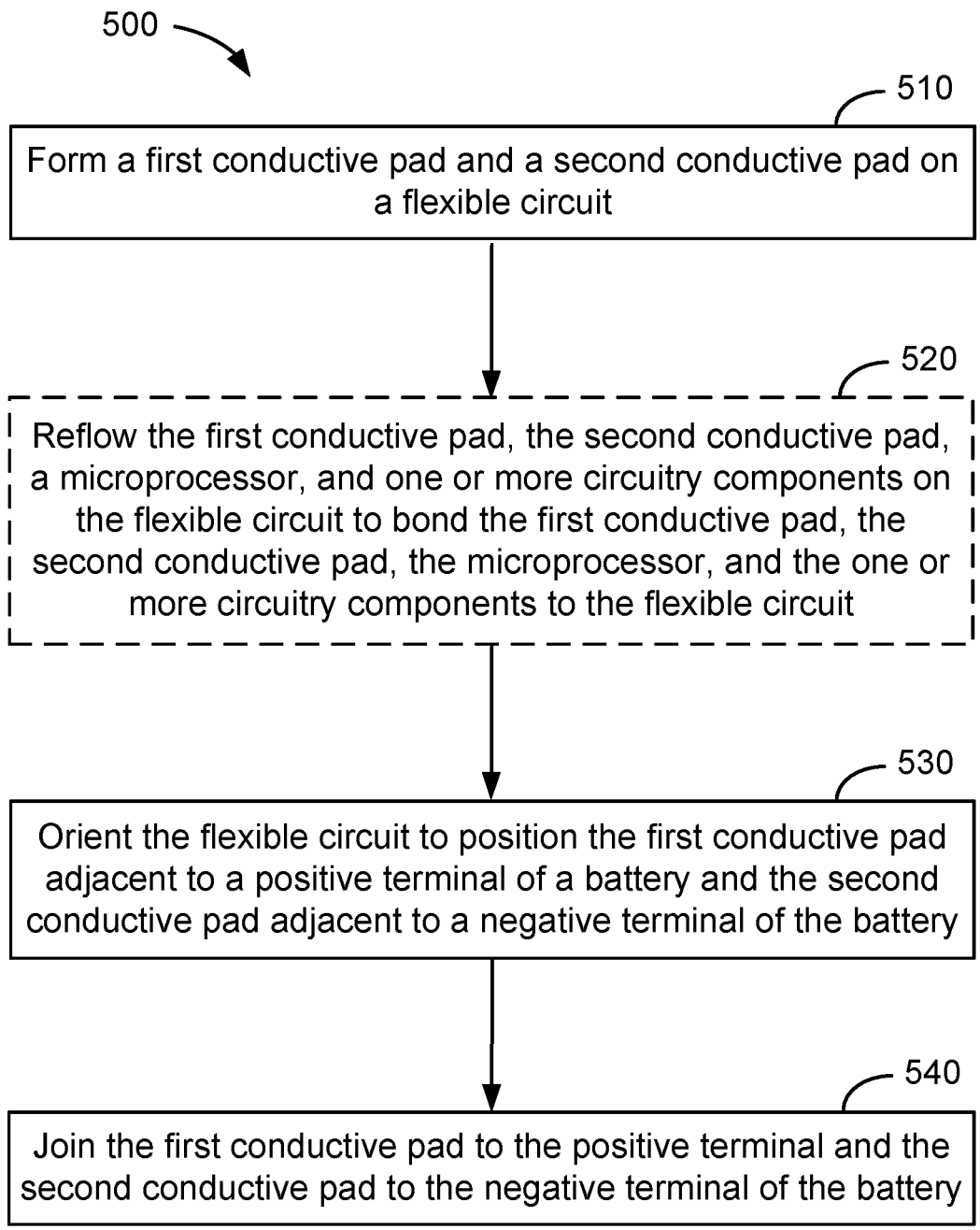
FIG. 5 is a flow diagram illustrating an example method of connecting a flexible circuit to a battery according to some implementations.

FIG. 5 is a flow diagram illustrating an example method of connecting a flexible circuit to a battery according to some implementations. The process 500 may be performed in a different order or with different, fewer, or additional operations.

At block 510 of the process 500, a first conductive pad and a second conductive pad are formed on a flexible circuit. The flexible circuit can include a flexible substrate capable of bending, folding, shaping, or conforming to a desired shape. In some implementations, the first and second conductive pads may be mounted on the flexible circuit, and the first and second conductive pads may be reflowed to bond the first and second conductive pads to the flexible circuit. In some implementations, the flexible circuit is provided with one or more holes. The flexible circuit may be fabricated with one or more holes already provided, and no additional operation is necessary for forming holes during assembly. However, in some implementations, the process 500 may further include forming one or more holes in the flexible circuit. Mounting the first and second conductive pads can include covering the one or more holes with the first and second conductive pads. The one or more holes may serve, for example, to permit resistance welding of the first and second conductive pads through the one or more holes. This enables direct bonding of the first and second conductive pads to a battery. In some implementations, the first and second conductive pads are symmetric about an axis of symmetry dividing the flexible circuit into two congruent halves. In some implementations, the first conductive pad includes a first SMT bond pad soldered on the flexible circuit and the second conductive pad includes a second SMT bond pad soldered on the flexible circuit.

Optionally, at block 520 of the process 500, the first conductive pad, the second conductive pad, a microprocessor, and one or more circuitry components on the flexible circuit are reflowed to bond the first conductive pad, the second conductive pad, the microprocessor, and the one or more circuitry components to the flexible circuit. The first and second conductive pads may be mounted by an automated SMT process using a pick-and-place machine, and the first and second conductive pads may be reflowed using an IR reflow oven. A microprocessor and one or more circuitry components may undergo the same automated process and reflow operation as the first and second conductive pads. Specifically, forming the first and second conductive pads on the flexible circuit can include mounting the first and second conductive pads on the flexible circuit using a pick-and-place machine, and mounting the microprocessor and the one or more circuitry components on the flexible circuit using the same pick-and-place machine. The one or more circuitry components may include, for example, one or more SMDs. Reflowing the microprocessor and the one or more circuitry components may occur simultaneously with reflowing the first and second conductive pads. The reflow operation may heat the first and second conductive pads, the microprocessor, and the one or more circuitry components at a temperature equal to or greater than 150° C., equal to or greater than 200° C., equal to or greater than 250° C., equal to or greater than 300° C., or between about 150° C. and about 500° C.

At block 530 of the process 500, the flexible circuit is oriented to position the first conductive pad adjacent to a positive terminal of a battery and the second conductive pad adjacent to a negative terminal of the battery. The flexible circuit may be bent, folded, shaped, conformed, or otherwise oriented so that the first and second conductive pads overlap and contact or nearly contact the terminals of the battery. In some implementations, the first and second conductive pads may be adjacent to the extent that the first and second conductive pads are contacting the terminals of the battery or substantially close to the terminals of the battery. For example, the first and second conductive pads can be at least within about 1 mm of the terminals of the battery. In some implementations, the flexible circuit is bent in a U-shape so that the first conductive pad and the second conductive pad are inwardly facing towards the battery. In some implementations, the first and second conductive pads may be oriented so that they are contacting the positive terminal and negative terminal of the battery. In some implementations, the battery is a coin cell battery. In some implementations, the battery is a cylindrical battery.

At block 540 of the process 500, the first conductive pad is joined to the positive terminal and the second conductive pad is joined to the negative terminal of the battery. In some implementations, having the first and second conductive pads joined to the positive and negative terminal, respectively, of the battery includes having the first and second conductive pads directly bonded, welded, or fused to the terminals of the battery. In some implementations, joining the first conductive pad to the positive terminal and the second conductive pad to the negative terminal includes laser welding, arc welding, or resistance welding the first conductive pad to the positive terminal and the second conductive pad to the negative terminal. The first and second conductive pads may be welded through one or more holes in the flexible circuit. In some implementations, the first conductive pad includes a first SMT bond pad soldered on the flexible circuit and directly bonded to the positive terminal of the battery, and the second conductive pad includes a second SMT bond pad soldered on the flexible circuit and directly bonded to the negative terminal of the battery. The first conductive pad and the second conductive pad may be directly bonded to the terminals of the battery without soldering or applying an adhesive.

The various illustrative logics, logical blocks, modules, circuits and algorithm steps described in connection with the implementations disclosed herein may be implemented as electronic hardware, computer software, or combinations of both. The interchangeability of hardware and software has been described generally, in terms of functionality, and illustrated in the various illustrative components, blocks, modules, circuits and steps described above. Whether such functionality is implemented in hardware or software depends upon the particular application and design constraints imposed on the overall system.

The hardware and data processing apparatus used to implement the various illustrative logics, logical blocks, modules and circuits described in connection with the aspects disclosed herein may be implemented or performed with a general purpose single- or multi-chip processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, such as a combination of a DSP and a microprocessor, a plurality of microprocessors, one or more microprocessors in conjunction with a DSP core, or any other such configuration. In some implementations, particular steps and methods may be performed by circuitry that is specific to a given function.

The functions in the various embodiments may be implemented in hardware, software, firmware, or any combination thereof. If implemented in software, the functions may be stored as one or more instructions or code on a non-transitory computer-readable medium or non-transitory processor-readable medium. The operations of a method or algorithm disclosed herein may be embodied in a processor-executable software module that may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable medium and/or computer-readable medium, which may be incorporated into a computer program product.

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein. Additionally, a person having ordinary skill in the art will readily appreciate, the terms "upper" and "lower," "top" and "bottom" "above" and "below," "over" and "under" and the like are sometimes used for ease of describing the figures, and indicate relative positions corresponding to the orientation of the figure on a properly oriented page, and may not reflect the proper orientation of a display element as implemented.

Certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, a person having ordinary skill in the art will readily recognize that such operations need not be performed in the particular order shown or in sequential order, or that all illustrated operations be performed, to achieve desirable results. Further, the drawings may schematically depict one more example processes in the form of a flow diagram. However, other operations that are not depicted can be incorporated in the example processes that are schematically illustrated. For example, one or more additional operations can be performed before, after, simultaneously, or between any of the illustrated operations. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products. Additionally, other implementations are within the scope of the following claims. In some cases, the actions recited in the claims can be performed in a different order and still achieve desirable results.

What is claimed is:

1. A system comprising:
   a battery having a positive terminal and a negative terminal; and a flexible circuit including a first conductive pad and a second conductive pad, the flexible circuit oriented to contact the first conductive pad to the positive terminal and the second conductive pad to the negative terminal of the battery, wherein the first conductive pad and the second conductive pad i) are symmetric about an axis of symmetry dividing the flexible circuit into two congruent halves, ii) include a first surface mount technology (SMT) bond pad and a second SMT bond bad, respectively, attached the flexible circuit, and iii) cover one or more holes in the flexible circuit, and wherein the first SMT bond pad is directly bonded to the positive terminal of the battery and the second SMT bond pad is directly bonded to the negative terminal of the battery, and wherein the flexible circuit is folded in a shape so that the first SMT bond pad and the second SMT bond pad are inwardly facing towards the battery.

2. The system of claim 1, wherein the first conductive pad and the second conductive pad are bonded to the flexible circuit using a reflow operation.

3. The system of claim 1, wherein the flexible circuit includes a microprocessor and one or more circuitry components, wherein the first conductive pad, the second conductive pad, the microprocessor, and the one or more circuitry components are formed on a surface of the flexible circuit that is inwardly facing towards the battery.

4. The system of claim 1, wherein each of the first and the second conductive pads are soldered to the flexible circuit.

5. The system of claim 1, wherein each of the first conductive pad and the second conductive pad are soldered to the flexible circuit and welded to the battery to form connections with the positive terminal and the negative terminal, respectively.

6. The system of claim 1, wherein the battery includes a coin cell battery.

7. The system of claim 1, wherein the battery includes a cylindrical battery.

8. A system comprising:
a battery having a positive terminal and a negative terminal;
a flexible circuit having one or more holes;
a first surface mount technology (SMT) bond pad soldered on the flexible circuit and directly bonded to the positive terminal of the battery; and
a second SMT bond pad soldered on the flexible circuit and directly bonded to the negative terminal of the battery, wherein the first and the second SMT bond pads cover the one or more holes, and wherein the first SMT bond pad and the second SMT bond pad are symmetric about an axis of symmetry dividing the flexible circuit into two congruent halves, and wherein the flexible circuit is folded in a shape so that the first SMT bond pad and the second SMT bond pad are inwardly facing towards the battery.

9. The system of claim 8, wherein the first SMT bond pad is resistance welded to the positive terminal of the battery and the second SMT bond pad is resistance welded to the negative terminal of the battery.

10. A method of connecting a flexible circuit to a battery, the method comprising:
forming a first conductive pad and a second conductive pad on the flexible circuit, wherein the first conductive pad and the second conductive pad are symmetric about an axis of symmetry dividing the flexible circuit into two congruent halves and wherein the first and second conductive pads cover one or more holes in the flexible circuit;
orienting the flexible circuit to position the first conductive pad adjacent to and contacting a positive terminal of the battery and the second conductive pad adjacent to and contacting a negative terminal of the battery such that the first and second conductive pads are inwardly facing toward the battery when the flexible circuit is bent in a U-shape; and
joining the first conductive pad to the positive terminal of the battery and the second conductive pad to the negative terminal of the battery.

11. The method of claim 10, wherein the flexible circuit includes one or more surface mount devices (SMDs) and a microprocessor, wherein the method further comprises reflowing the first conductive pad, the second conductive pad, the microprocessor, and the one or more SMDs to bond the first conductive pad, the second conductive pad, the microprocessor, and the one or more SMDs to the flexible circuit.

12. The method of claim 10, wherein joining the first conductive pad to the positive terminal and the second conductive pad to the negative terminal includes a process selected from the group consisting of: laser welding, arc welding, and resistance welding.

13. The method of claim 10, wherein forming the first conductive pad and the second conductive pad on the flexible circuit comprises mounting the first conductive pad and the second conductive pad on the flexible circuit using a pick-and-place machine.

14. The method of claim 10, wherein the battery includes a cylindrical battery.

15. The method of claim 10, wherein the battery includes a coin cell battery.

16. The method of claim 11, wherein the first conductive pad and the second conductive pad are bonded to the flexible circuit simultaneous with the one or more SMDs and the microprocessor.

17. The method of claim 11, wherein reflowing the first conductive pad, the second conductive pad, the microprocessor, and the one or more SMDs occur at a temperature equal to or greater than about 150° C.

18. The method of claim 13, further comprising:
mounting a microprocessor and one or more circuitry components on the flexible circuit simultaneous with mounting the first conductive pad and the second conductive pad using the pick-and-place machine; and
reflowing the first conductive pad, the second conductive pad, the microprocessor, and the one or more circuitry components to bond the first conductive pad, the second conductive pad, the microprocessor, and the one or more circuitry components to the flexible circuit.

* * * * *